(12) United States Patent
Monroe et al.

(10) Patent No.: US 12,263,071 B2
(45) Date of Patent: Apr. 1, 2025

(54) PLANT-BASED ABSORBENT ARTICLE

(71) Applicant: KUDOS INNOVATIONS, INC., Los Angeles, CA (US)

(72) Inventors: Emily Monroe, Georges Mills, NH (US); Amrita Saigal, Cambridge, MA (US); John Poccia, Monmouth Beach, NJ (US); James Keighley, Cedarville, MI (US)

(73) Assignee: KUDOS INNOVATIONS, INC., Los Angeles, CA (US)

( * ) Notice: Subject to any disclaimer, the term of this patent is extended or adjusted under 35 U.S.C. 154(b) by 424 days.

(21) Appl. No.: 17/240,736

(22) Filed: Apr. 26, 2021

(65) Prior Publication Data

US 2021/0330519 A1    Oct. 28, 2021

Related U.S. Application Data

(60) Provisional application No. 63/015,969, filed on Apr. 27, 2020.

(51) Int. Cl.
*A61F 13/511* (2006.01)
*A61F 13/15* (2006.01)
(Continued)

(52) U.S. Cl.
CPC .. *A61F 13/51121* (2013.01); *A61F 13/15252* (2013.01); *A61F 13/47* (2013.01);
(Continued)

(58) Field of Classification Search
CPC .... A61F 13/15252; A61F 13/47; A61F 13/49; A61F 13/51121; A61F 13/537; A61F 2013/15959; A61F 2013/530868
See application file for complete search history.

(56) References Cited

U.S. PATENT DOCUMENTS 3,929,135 A * 12/1975 Thompson ................ B32B 3/28
                                                    604/374
4,324,246 A *  4/1982 Mullane ................ A61F 13/512
                                                    604/371
(Continued)

FOREIGN PATENT DOCUMENTS

MU    9101469-7     *  7/2011  ............. A61F 13/15
MX    350246 B         8/2017
(Continued)

OTHER PUBLICATIONS

Nonwovens Industry Features Focus on: Raw Materials, Jun. 5, 2019, https://www.nonwovens-industry.com/issues/2019-06/view_features/focus-on-raw-materials/#:~:text=Pulcra%20has%20developed%20two%20new%20products%20that%20offer,can%20be%20sprayed%20or%20padded%20onto%20a%20nonwoven.*
(Continued)

*Primary Examiner* — Michele Kidwell
(74) *Attorney, Agent, or Firm* — Rothwell, Figg, Ernst & Manbeck, P.C.

(57) ABSTRACT

An absorbent article that is toxin-free and made from plant-based, biobased, all natural, clean ingredients. In one embodiment, the absorbent article is a diaper made from plant-based resin, comprising: (i) a first layer, wherein the first layer is a cotton top sheet with a wax-based coating deposited on an exterior surface of the first layer (adjacent to the wearer's skin, or "user-facing"); and (ii) a second layer, wherein the second layer is an acquisition/distribution layer (ADL), and wherein the ADL is comprised of two sub-layers of different materials, a first sublayer comprising an apertured film acquisition sub-layer disposed on top of, and laminated to, a second sub-layer comprising a nonwoven acquisition layer.

20 Claims, 7 Drawing Sheets

(51) Int. Cl.
    *A61F 13/47*    (2006.01)
    *A61F 13/49*    (2006.01)
    *A61F 13/53*    (2006.01)
(52) U.S. Cl.
    CPC .... *A61F 13/49* (2013.01); *A61F 2013/15959* (2013.01); *A61F 2013/530868* (2013.01)

(56) References Cited

U.S. PATENT DOCUMENTS

| | | | |
|---|---|---|---|
| 5,368,909 A * | 11/1994 | Langdon | B26F 1/26 |
| | | | 428/137 |
| 5,603,707 A * | 2/1997 | Trombetta | A61F 13/53743 |
| | | | 604/383 |
| 6,319,239 B1 * | 11/2001 | Daniels | A61F 13/539 |
| | | | 604/385.01 |
| 6,455,753 B1 | 9/2002 | Glaug et al. | |
| 6,509,513 B2 | 1/2003 | Glaug et al. | |
| 6,515,195 B1 * | 2/2003 | Lariviere | A61F 13/15203 |
| | | | 604/383 |
| 6,566,578 B1 | 5/2003 | Glaug et al. | |
| 6,610,904 B1 | 8/2003 | Thomas et al. | |
| 6,700,036 B2 | 3/2004 | Thomas et al. | |
| 7,204,907 B2 | 4/2007 | Cree et al. | |
| 7,378,568 B2 | 5/2008 | Thomas et al. | |
| 8,383,227 B2 | 2/2013 | Seyler et al. | |
| 8,653,323 B2 | 2/2014 | Schmidt et al. | |
| 8,669,410 B2 | 3/2014 | Weismantel et al. | |
| 9,216,117 B2 | 12/2015 | Hwang et al. | |
| 9,642,754 B2 | 5/2017 | Andersson et al. | |
| 9,750,651 B2 | 9/2017 | Bianchi et al. | |
| 9,814,634 B2 | 11/2017 | Schröder et al. | |
| 10,258,517 B1 | 4/2019 | Mashino et al. | |
| 10,500,108 B1 | 12/2019 | Mashino et al. | |
| 11,364,154 B2 | 6/2022 | Yamada | |
| 2001/0027302 A1 | 10/2001 | Glaug et al. | |
| 2002/0064639 A1 * | 5/2002 | Rearick | B32B 9/02 |
| | | | 428/292.1 |
| 2004/0176733 A1 | 9/2004 | Glaug et al. | |
| 2007/0073254 A1 * | 3/2007 | Ponomarenko | A61F 13/53713 |
| | | | 604/383 |
| 2014/0276512 A1 * | 9/2014 | Cheng | A61L 15/34 |
| | | | 604/366 |
| 2016/0220427 A1 | 8/2016 | Ducker | |
| 2017/0021051 A1 * | 1/2017 | Richards | A61F 13/53409 |
| 2018/0140469 A1 | 5/2018 | Kane et al. | |
| 2019/0380878 A1 * | 12/2019 | Edwards | A61F 13/00012 |
| 2020/0138642 A1 * | 5/2020 | Wagner | A61F 13/476 |
| 2021/0045943 A1 * | 2/2021 | Blasius | A61F 13/8405 |

FOREIGN PATENT DOCUMENTS

| | | |
|---|---|---|
| WO | 2007/106929 A1 | 9/2007 |
| WO | 2018004564 A1 | 1/2018 |
| WO | 2019/118987 A1 | 6/2019 |

OTHER PUBLICATIONS

International Search Report and the Written Opinion of the International Searching Authority, issued in corresponding International Application No. PCT/US2021/029165, dated Aug. 17, 2021, 15 pages.
International Preliminary Report on Patentability issued in PCT/US2021/029165 on Oct. 27, 2022, 9 pages.
The extended European search report mailed Apr. 18, 2024 in corresponding European Patent Application No. 21795833.9 (6 pages).

* cited by examiner

PLANT-BASED ABSORBENT ARTICLE

CROSS REFERENCE TO RELATED APPLICATION(S)

This application claims the benefit of U.S. Provisional Application No. 63/015,969, filed Apr. 27, 2020, the disclosure of which is incorporated herein by reference in its entirety

TECHNICAL FIELD

Aspects of this disclosure relate to absorbent articles and, more particularly, to an absorbent article, such as, for example, a diaper, that is toxin-free and made from plant-based, biobased, renewable, all natural, clean ingredients.

BACKGROUND

Most absorbent products sold in the United States are comprised of layers of single use plastic materials bonded together through the application of heat and pressure. These plastic materials commonly include polypropylene (PP), polyethylene (PE), polyethylene terephthalate (PET) and polyester. Absorbent products designed with these materials are typically superior in performance to the cloth absorbent products used in previous generations. The performance advantage comes from material and construction designed to quickly get moisture away from the skin. Moisture in contact with skin for sustained periods of time can lead to undesired effects, ranging from mild skin irritation to dermatitis or eczema, so disposable plastic absorbent products that reduce moisture and moisture's downstream effects make these products widely accepted in the American marketplace. However, many consumers are choosing to purchase products made from renewable materials due to concerns around potential health risks with petro-chemical derived materials, material disposal, and desire for sustainably sourced products.

SUMMARY

Renewable materials available today include cotton, bamboo in the form of viscose, hemp, cellulose from wood pulp, plastics from plant-derived polymers such as "green" polyethylene or polypropylene, and plant-based plastics, such as polylactic acid (PLA). Consumer demand for the use of more plant fibers, specifically cotton and bamboo, leads to the use of those fibers in the components of absorbent articles that come into contact with the user's skin, including the top sheet or liner and the back sheet or cover. These natural fibers have high cellulose content, giving them excellent absorbent properties. However, the use of a hydrophobic natural fiber in the top sheet (user-facing surface) of an absorbent article, such as a diaper or a sanitary pad, can be problematic, as the moisture absorbed and retained in the fabric can cause skin irritation if the moisture is not removed quickly from the user's skin.

Various techniques have been proposed to enhance the performance of top sheet fabrics made of natural fibers by addressing moisture removal in the layers beneath the top sheet. Such techniques, however, do not disclose the use of plant-based or renewable materials in the layers beneath the top sheet, including the fluid transfer layers, acquisition and distribution layers.

Thus, there remains a need for an absorbent article that combines consumer demand for plant-based fibers in the user-facing top sheet layers with the technology enhancements that allow for better fluid migration to the absorbent core configured to use plant-based materials for the acquisition distribution layers, without the use of petro-chemical derived materials.

Advantages of using plant-based fibers in, for example, the diaper industry may include replacing 585 million pounds of plastic with unbleached natural fibers such as cotton, and $2 billion pounds of fossil-fuel derived diaper materials could instead be sourced from renewable materials each year.

Described herein are various embodiments for a plant-based absorbent article.

According to one embodiment, an absorbent article is provided that is chemical-free and made from plant-based, biobased, natural ingredients. In one embodiment, the absorbent article is a diaper made from plant-based resin, comprising: (i) a first layer, wherein the first layer is a cotton top sheet with a wax-based coating deposited on an exterior surface of the first layer (adjacent to the wearer's skin, or "user-facing"); and (ii) a second layer, wherein the second layer is an acquisition/distribution layer (ADL), and wherein the ADL is comprised of two sub-layers of different materials, a first sublayer comprising an apertured film acquisition sub-layer disposed on top of, and laminated to, a second sub-layer comprising a non-woven distribution layer designed to rapidly distribute liquid from the first layer through the acquisition layer into the absorbent core.

Embodiments disclosed herein include a layer structure of an absorbent article that includes (i) a first layer, wherein the first layer is a cotton top sheet with a wax-based coating deposited on an exterior surface of the first layer (adjacent to the wearer's skin, or "user-facing"); and (ii) a second layer, wherein the second layer is an acquisition/distribution layer (ADL), and wherein the ADL is comprised of two sub-layers of different materials, a first sublayer comprising an apertured film acquisition sub-layer disposed on top of, and laminated to, a second sub-layer comprising a non-woven distribution. The layers of the layer structure of the absorbent article of the embodiments disclosed herein are made from plant-based materials and without the use of petro-chemical derived materials. In some embodiments, the layers of the layer structure of the absorbent article are at least 70% plant-based, at least 75% plant-based, at least 80% plant-based, at least 85% plant-based, at least 90% plant-based, and, most preferably, at least 95% plant-based.

In some embodiments, the absorbent article is laminated to an absorbent core and liquid impermeable barrier and covered with a nonwoven material. The absorbent core may be created with a combination of cellulose fluff pulp that is intended to rapidly acquire moisture in combination with sodium polyacrylate. The sodium polyacrylate is intended to retain moisture, though it absorbs the moisture slower than the fluff pulp part of the core. These two absorbent media work in tandem to quickly then robustly trap moisture in the core of the absorbent article, preventing moisture from coming back into contact with skin. This absorbent core may be wrapped in a thin layer of either cellulose or nonwoven material and adhered on one side to the acquisition distribution layer and on the opposite side to a liquid impermeable barrier to retain moisture inside the diaper. This barrier may, in turn, be covered in a nonwoven material, which may be comprised of polypropylene, polyethylene, or cotton blend, to provide softness to the outside of the absorbent article.

In some embodiments, the apertured film layer of the ADL used in the absorbent product may be, for example, a film product called "AquiDry" available from Tredegar Films Product Corporation and Fitesa Film Products, LLC.

In some embodiments, other higher cellulose content natural fibers may be used in the top sheet, including blends of hemp, flax, and wool. Additionally, the acquisition distribution layer may be formed from a single layer of a formed film made from plant-based resins or a through-air bonded nonwoven material made from plant-based resins.

In one embodiment, the absorbent article is a baby diaper, including open-style construction for daytime and nighttime use, training pants construction, and swim diapers. In other embodiments, the absorbent article may be, but is not limited to, one or more of the following: an adult incontinence product, a feminine hygiene absorbent pad and/or postpartum absorbent product, a pants-style absorbent feminine hygiene product, a disposable changing pad, or a pet absorbent pad.

The above and other aspects and embodiments are described below with reference to the accompanying drawings.

BRIEF DESCRIPTION OF THE DRAWINGS

The accompanying drawings, which are incorporated herein and form part of the specification, illustrate various embodiments of the present disclosure and, together with the description, further serve to explain the principles of the disclosure and to enable a person skilled in the pertinent art to make and use the embodiments disclosed herein. In the drawings, like reference numbers indicate identical or functionally similar elements.

DETAILED DESCRIPTION

In accordance with embodiments disclosed herein, a new absorbent article is introduced, which is toxin-free and made from plant-based, biobased, renewable, all natural, clean ingredients. In one embodiment, the absorbent article is a diaper made from plant-based resin, comprising: (i) a first layer, wherein the first layer is a cotton top sheet with a wax-based coating deposited on an exterior surface of the first layer (adjacent to the wearer's skin, or "user-facing")); and (ii) a second layer, wherein the second layer is an acquisition/distribution layer (ADL), and wherein the ADL is comprised of two sub-layers of different materials, a first sublayer comprising an apertured film acquisition sub-layer disposed on top of, and laminated to, a second sub-layer comprising a non-woven distribution layer. The first sublayer may be made of a vacuum formed film, a blown film, a hydroformed film or any other manufacturing method that results in a plant-based apertured film.

Figure 1:
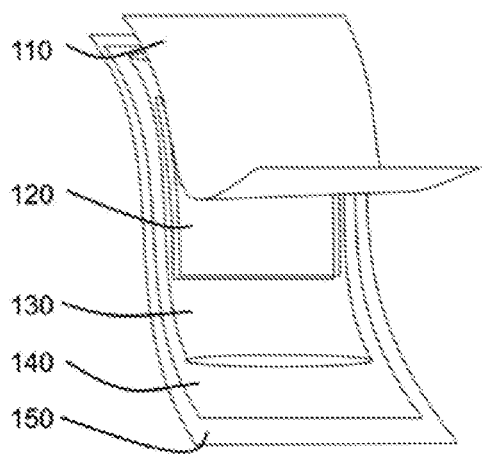
FIG. 1 illustrates an absorbent article in accordance with some embodiments.

For example, and referring now to FIG. 1, the absorbent article includes a first layer depicted as item 110 made of cotton or another natural, high-cellulose nonwoven material about 30 to 40 grams per square meter in density. In some embodiments, the cotton of layer 110 may be 100% unbleached, mechanically cleaned cotton. Layer 110 may include up to 30% of its weight as a fiber that will bond ultrasonically to any other sublayers and which may include polypropylene, polyethylene, polylactic acid, or polyester. Layer 110 may include up to 30% of its weight as a blend of scoured and hydrogen peroxide bleached cotton to provide increased machine direction yield strength in the spunlacing process. The 70-100% of layer 110 made of unbleached, mechanically cleaned cotton retains natural waxes in the cotton, providing hydrophobicity not found in typical chlorine-bleached cotton. In one embodiment, layer 110 may appear as a flat or non-apertured nonwoven fabric. In other embodiments layer 110 may display a pattern of perforations or apertures which vary in shape and size but may include oval, circular, or squared holes ranging from 0.006 inches to 0.020 inches across. In one embodiment, layer 110 is coated with a wax-based hydrophobic substrate, such as, for example, with the wax repellent available from Pulcra Chemicals sold as "Stantex Rep T™" that allows fluid to pass quickly through the material. In other embodiments, layer 110 may remain uncoated.

Layer 120 is a composite of two materials that are bonded to layer 110 and serve as an acquisition and distribution layer (ADL) for fluid. The bonding between layers 110 and 120 in one embodiment is achieved through adhesives applied at a rate of between 0.25-5 grams per square meter. In other embodiments, layer 110 may be bonded to layer 120 through an ultrasonic or needle-punch bond. Layer 120 is a composite of two materials that may be bonded by adhesive in one embodiment, or by vacuum form lamination or ultrasonic bonding in other embodiments. The two materials in layer 120 may be a polyethylene film made from plant based resin and a nonwoven produced from polylactic acid staple fibers.

In other embodiments, the materials in layer 120 may be a polypropylene film or a film made up of both polypropylene and polyethylene, and the nonwoven component may be produced from another natural, plant-derived, or recycled staple fiber that may contain polypropylene or polyethylene terephthalate, up to 30% by weight.

In some embodiments, the film component of layer 120 includes a pattern of perforations forming funnels oriented away from layer 110 with the purpose of allowing fluid to quickly exit layer 110 through layer 120 into the absorbent core, shown in FIG. 1, as layer 130. The pattern of perforations may be configured as an arrangement of circular, oval, and/or rhomboid holes ranging in size from 0.005 inches in diameter up to 0.05 inches in diameter. The perforations may be arranged in a grid, with between 30-120 holes per square inch. In other embodiments, the perforations on the film component of layer 120 may form other patterns, including waveforms, stars, flowers, and the like. The nonwoven component of layer 120 is a highly porous material made by through-air bonding with a density of 60 grams per square meter. In other embodiments, this component may range from 30-100 grams per square meter in density, and the material may be made in other ways, including by spunbonding, airlaid or carding and bonding.

one purpose of layer 120 is to move fluid from layer 110 through layer 120 into the absorbent core in layer 130. The absorbent core is formed by an inner layer and an outer layer. In one embodiment, the outer layer is a nonwoven material made from cellulose, and the inner layer is a mixture of cellulose fluff and super absorbent polymer (SAP). This SAP may be made from plant-based acrylic acid. In other embodiments, the outer layer may be made of polylactic acid, polypropylene, recycled polyester, or a mixture of those materials. One purpose of layer 130 is to trap fluid through a fast-absorbing but low-retaining medium in the cellulose fluff, and to trap fluid through a slow-absorbing but high-retaining medium in the SAP. Layer 130 is referred to as the "core" of the absorbent article. The core is bonded to layer 140 through adhesive bonding in the exemplary embodiment, or through ultrasonic bonding in other embodiments.

Layer 140 may be comprised of a breathable polyethylene film made of at least 70% plant based resin. In other embodiments, layer 140 may be made of a plant based polylactic acid breathable film. In some embodiments, this film is between 13 and 20 grams per square meter in density, with microporous holes to allow vapor to pass through the film. One purpose of layer 140 is to contain the fluid that is to be absorbed in the core of the article while allowing air to transfer between the outside environment and the inner layers of the article. Air circulation allowed by the breathable film in layer 140 works to prevent fluid buildup which can cause skin irritation or dermatitis. Layer 140 is bonded to layer 150 through adhesive bonding in the exemplary embodiment, or through ultrasonic bonding in other embodiments.

Layer 150 may be comprised of a nonwoven material made of polyethylene from plant based resin. In other embodiments, layer 150 may be made of a cotton material or a bicomponent of two resins that may be either polypropylene and polyethylene, or polyethylene and polylactic acid, with plant based resins making up more than 10% by weight of the material. The nonwoven material is between 12 and 35 grams per square meter in density. The fibers in layer 150 may be either mechanically or heat bonded with a pattern resembling a honeycomb, a grid, or another similar pattern. one purpose of layer 150 is to provide a positive tactile experience for the user of the absorbent article, and layer 150 should feel soft to the touch.

Figure 2:
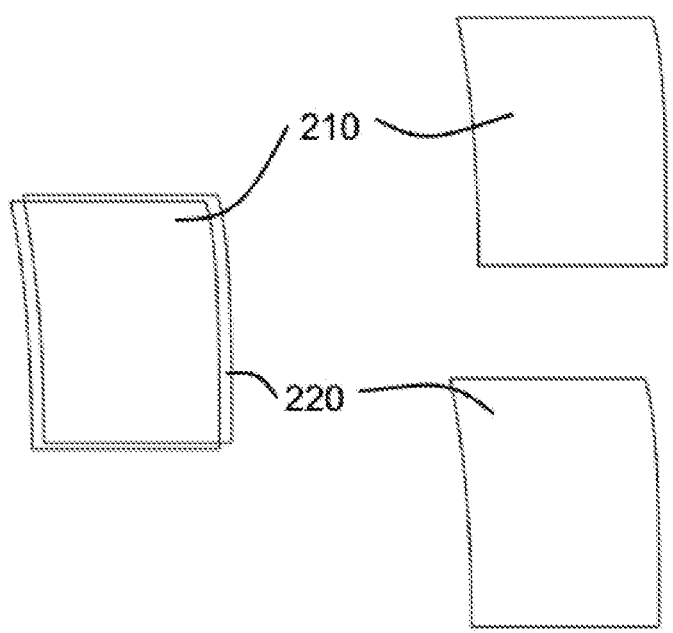
FIG. 2 is a schematic diagram of the layer structure of an absorbent article in accordance with some embodiments.

Referring now to FIG. 2, the two materials that make up the acquisition distribution layer (ADL) (layer 120 in FIG. 1) are shown. According to some embodiments, layer 210 is a polyethylene film made from plant based resin and layer 220 is a nonwoven produced from polylactic acid staple fibers. In other embodiments, the material in layer 210 may be a polypropylene film, a polylactic acid film, or a film made up of both polypropylene and polyethylene, and the nonwoven component in layer 220 may be produced from another natural, plant-derived, or recycled staple fiber that may contain polypropylene, up to 30% by weight. Layer 210 and layer 220 may be bonded together through adhesive bonding to form one continuous web of composite or laminated material. In other embodiments, particularly in embodiments where polypropylene is present in any amount in both layer 210 and layer 220, the two layers may be bonded together by vacuum form lamination or ultrasonic bonding.

Figure 3:
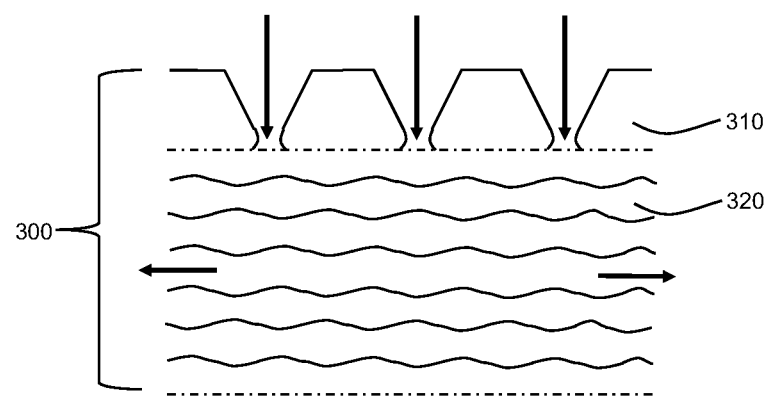
FIG. 3 is a schematic diagram of two sub-layers of different materials of an acquisition/distribution layer (ADL) of an absorbent article in accordance with some embodiments.

Referring now to FIG. 3, item 300 shows in cross section the acquisition distribution layer (layer 120 in FIG. 1) that is made up of a composite of two materials. As depicted in FIG. 3, the two layers of item 300 are layer 310, a polyethylene film made from plant based resin, and layer 320, a nonwoven produced from polylactic acid staple fibers. In other embodiments, the material in layer 310 may be a polypropylene film, a polylactic acid film, or a film made up of both polypropylene and polyethylene, and the nonwoven component in layer 320 may be produced from another natural, plant-derived, or recycled staple fiber that may contain polypropylene, up to 30% by weight.

In the cross section shown in FIG. 3, the perforations of layer 310 are visible. These perforations form funnels oriented with the purpose of allowing fluid to quickly exit layer 310 through layer 320 into the absorbent core, shown in FIG. 1 as layer 130. The direction of fluid flow is shown in FIG. 3 to be down through the cones and into the nonwoven layer 320, where fluid is distributed along the length of the material and over a substantial area of the absorbent core. In some embodiments, layer 320 is a through air bonded nonwoven with air pockets distributed randomly throughout the material volume. These air pockets allow for fluid to flow easily through layer 320 in both directions, through and across the material. The funnels of layer 310 form a circuitous path for fluid flow, preventing fluid from easily flowing back from layer 320 through layer 310 onto the layer above, shown in FIG. 1 as layer 110, which is in contact with the user's skin. Preventing fluid flow back onto the user's skin provides for benefits in reducing and preventing skin irritation or dermatitis.

In some embodiments, the cotton material shown as layer 110 is adhesively bonded to subsequent layers, including layers 310 and 320. Cotton and other natural cellulose fibers will not ultrasonically bond to typical blends of nonwoven materials made, for example, of polyethylene and polypropylene. Cotton and other natural cellulose materials can be up to seven times more absorbent than typical synthetic polypropylene or polyethylene nonwoven materials. Embodiments of the absorbent article disclosed herein are, therefore, able to achieve enhanced performance through the novel combination of layers 310 and 320 with a natural material in layer 110.

The layers of the layer structure of the absorbent article of the embodiments disclosed herein are made from plant-based materials and without the use of petro-chemical derived materials. In some embodiments, the layers of the layer structure of the absorbent article are at least 70% plant-based, at least 75% plant-based, at least 80% plant-based, at least 85% plant-based, at least 90% plant-based, and, most preferably, at least 95% plant-based.

Figure 4:
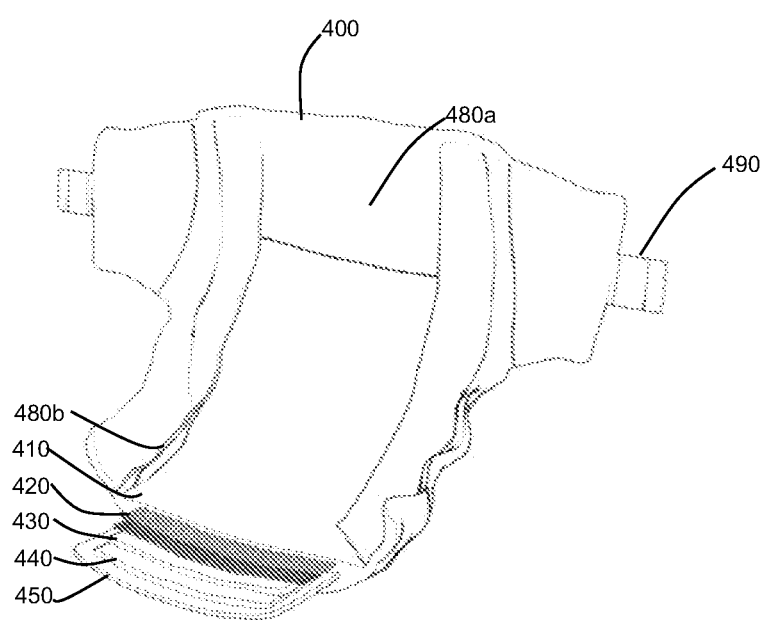
FIG. 4 illustrates an absorbent article configured in the form of a diaper, according to some embodiments.

Referring now to FIG. 4, an absorbent article for use in a diaper is shown. Diaper 400 may include layers 410, 420, 430, 440, and 450, which correspond to layers 110, 120, 130, 140, and 150, respectively, of FIG. 1. FIG. 4 additionally depicts elastic at the waistband 480a and leg cuffs 480b, as well as tab 490 for securing the diaper 400 around the waist. In some embodiments, the diaper (400) shown in FIG. 4 is made entirely of renewable plant based sources.

Figure 5:
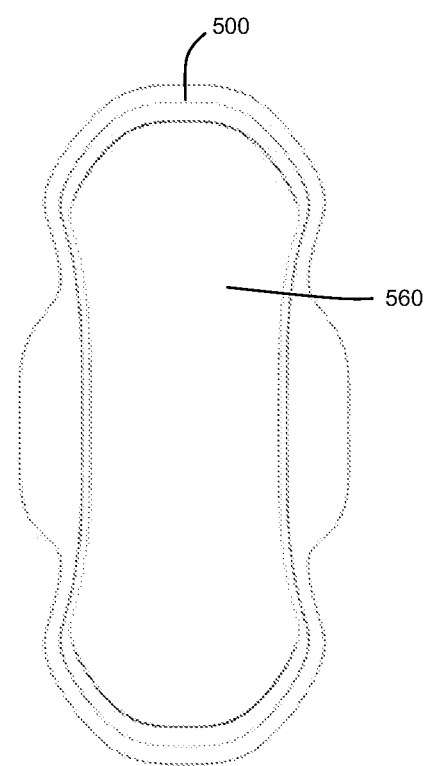
FIG. 5 illustrates an absorbent article configured in the form of a feminine hygiene product, according to some embodiments.

Referring now to FIG. 5, an absorbent article configured in the form of a feminine hygiene product 500, according to some embodiments, is shown. Product 500 may be, for example, a feminine hygiene absorbent pad, a postpartum absorbent product or the like. Product 500 may include an absorbent article 560 according to the embodiments disclosed herein. Absorbent article 560 may comprise, for example, the absorbent article with layers shown in FIG. 1.

Figure 6:
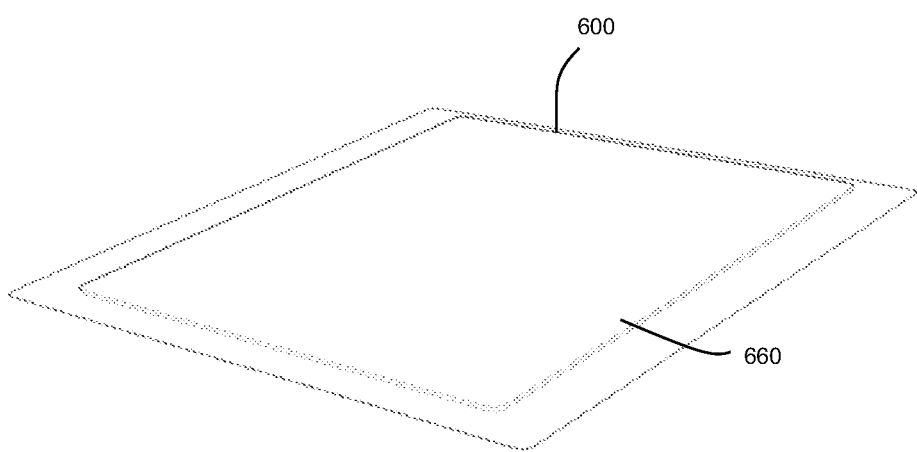
FIG. 6 illustrates an absorbent article configured in the form of a pad, according to some embodiments.

Referring now to FIG. 6, an absorbent article configured in the form of a pad 600, according to some embodiments, is shown. Pad 600 may be, for example, an absorbent pad for use with puppies or other animals, or a disposable changing pad. Pad 600 may include an absorbent article 660 according to the embodiments disclosed herein. Absorbent article 660 may comprise, for example, the absorbent article with layers shown in FIG. 1.

Figure 7:
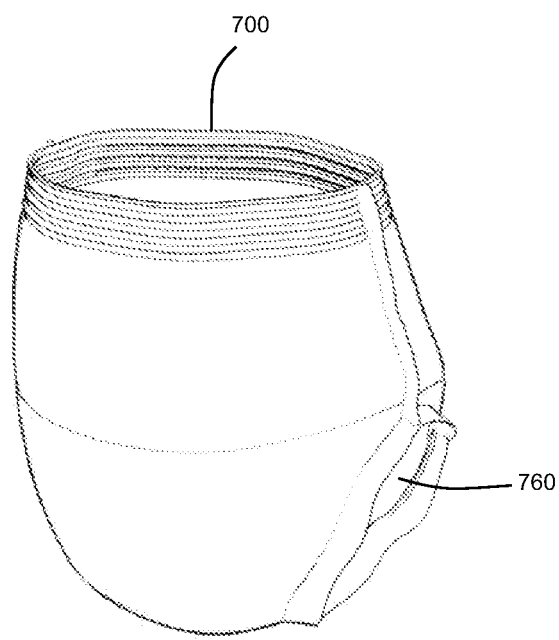
FIG. 7 illustrates an absorbent article configured in the form of an adult incontinence product, according to some embodiments.

FIG. 7 illustrates an absorbent article configured in the form of an adult incontinence product 700, according to some embodiments. Product 700 may be, for example, and adult diaper, a pants-style absorbent feminine hygiene product, or the like. Product 700 may include an absorbent article 760 according to the embodiments disclosed herein. Absorbent article 760 may comprise, for example, the absorbent article with layers shown in FIG. 1.

While various embodiments of the present disclosure are described herein, it should be understood that they have been presented by way of example only, and not limitation. Thus, the breadth and scope of the present disclosure should not be limited by any of the above-described embodiments. Generally, all terms used herein are to be interpreted according to their ordinary meaning in the relevant technical field, unless a different meaning is clearly given and/or is implied from the context in which it is used. All references to a/an/the article, element, apparatus, component, layer, means, step, etc. are to be interpreted openly as referring to at least one instance of the article, element, apparatus, component, layer, means, step, etc., unless explicitly stated otherwise. Any combination of the above-described elements in all possible variations thereof is encompassed by the disclosure unless otherwise indicated herein or otherwise clearly contradicted by context.

The invention claimed is:

1. A plant-based absorbent article comprising a plurality of layers, the plurality of layers consisting of:
   (i) a first layer having a first user-facing surface and a first non-user-facing surface, wherein the first layer is a top sheet consisting of 100% cotton providing a natural hydrophobic fiber layer adjacent to a user's skin and configured to allow fluid to rapidly pass through;
   (ii) a second layer having a second user-facing surface and a second non-user-facing surface, wherein the second user-facing surface is immediately adjacent to and in direct contact with the first non-user-facing surface with no intervening layers, and wherein the second layer is an acquisition/distribution layer (ADL) consisting of two sub-layers of different materials, wherein a first sub-layer is an apertured film acquisition layer and a second sub-layer is a non-woven distribution layer, wherein the first sub-layer is immediately adjacent to and in direct contact with the second sub-layer with no intervening sub-layers, and
   wherein the apertured film acquisition layer includes perforations that form funnels configured to provide a circuitous path for fluid flow and oriented to prevent fluid flow back towards the first layer;
   (iii) a third layer having a third user-facing surface and a third non-user-facing surface, wherein the third user-facing surface is immediately adjacent to and in direct contact with the second non-user-facing surface with no intervening layers, and wherein the third layer is an absorbent core configured to receive and trap the fluid flowing from the second layer; and
   (iv) a fourth layer having a fourth user-facing surface and a fourth non-user-facing surface, wherein the fourth user-facing surface is immediately adjacent to and in direct contact with the third non-user-facing surface with no intervening layers, wherein the fourth layer is a liquid impermeable barrier configured to contain the fluid received and trapped in the absorbent core while allowing air to transfer between the outside environment and the plurality of layers.

2. The absorbent article according to claim 1, wherein the article is a diaper.

3. The absorbent article according to claim 1, wherein the cotton top sheet is spunlace cotton.

4. The absorbent article according to claim 1, further including a wax-based coating deposited on the first user-facing surface.

5. The absorbent article according to claim 4, wherein the wax-based coating is hydrophobic.

6. The absorbent article according to claim 1, wherein the apertured film acquisition sub-layer is 95% biobased green polyethylene.

7. The absorbent article according to claim 1, wherein the non-woven distribution layer is a biodegradable and compostable fluid distribution layer through air bond polylactic acid (PLA).

8. A plant-based absorbent article comprising a plurality of layers, the plurality of layers consisting of:
   (1) a first layer having a first user-facing surface and a first non-user-facing surface, wherein the first layer is a top sheet consisting of 100% cotton providing a natural hydrophobic fiber layer adjacent to a user's skin and configured to allow fluid to rapidly pass through;
   (ii) a second layer having a second user-facing surface and a second non-user-facing surface, wherein the second user-facing surface is immediately adjacent to and in direct contact with the first non-user-facing surface with no intervening layers, and wherein the second layer is an acquisition/distribution layer (ADL) consisting of two sub-layers of different materials, wherein a first sub-layer is a non-woven distribution layer and a second sub-layer is an apertured film acquisition sub-layer, wherein the first sub-layer is immediately adjacent to and in direct contact with the second sub-layer with no intervening sub-layers, and
   wherein the apertured film acquisition sub-layer includes perforations that form funnels configured to provide a circuitous path for fluid flow and oriented to prevent fluid flow back towards the first layer;
   (iii) a third layer having a third user-facing surface and a third non-user-facing surface, wherein the third user-facing surface is immediately adjacent to and in direct contact with the second non-user-facing surface with no intervening layers, and wherein the third layer is an absorbent core configured to receive and trap the fluid flowing from the second layer; and
   (iv) a fourth layer having a fourth user-facing surface and a fourth non-user-facing surface, wherein the fourth user-facing surface is immediately adjacent to and in direct contact with the third non-user-facing surface with no intervening layers, wherein the fourth layer is a liquid impermeable barrier configured to contain the fluid received and trapped in the absorbent core while allowing air to transfer between the outside environment and the plurality of layers.

9. The absorbent article according to claim 8, wherein the article is a diaper.

10. The absorbent article according to claim 8, wherein the cotton top sheet is spunlace cotton.

11. The absorbent article according to claim 8, further including a wax-based coating deposited on the first user-facing surface.

12. The absorbent article according to claim 11, wherein the wax-based coating is hydrophobic.

13. The absorbent article according to claim 8, wherein the apertured film acquisition sub-layer is 95% biobased green polyethylene.

14. The absorbent article according to claim 8, wherein the non-woven distribution layer is a biodegradable and compostable fluid distribution layer through air bond polylactic acid (PLA).

15. The absorbent article according to claim 1, wherein the article is one of: an adult incontinence product, a feminine hygiene absorbent pad, a postpartum absorbent product, a pants-style absorbent feminine hygiene product, a disposable changing pad, or a pet absorbent pad.

16. The absorbent article according to claim 1, wherein the first layer and the second layer are at least 95% plant-based.

17. The absorbent article according to claim 1, wherein the first layer and the second layer are made from plant-based materials and without the use of petro-chemical derived materials.

18. The absorbent article according to claim 1, wherein the cotton used in the first layer includes a blend of scoured and hydrogen peroxide bleached cotton.

19. The absorbent article according to claim 1, wherein the cotton used in the first layer includes unbleached, mechanically cleaned cotton.

20. A plant-based absorbent article comprising a plurality of layers, the plurality of layers consisting of:
(i) a first layer having a first user-facing surface and a first non-user-facing surface, wherein the first layer is a top sheet consisting of 100% cotton providing a natural hydrophobic fiber layer adjacent to a user's skin and configured to allow fluid to rapidly pass through;
(ii) a second layer having a second user-facing surface and a second non-user-facing surface, wherein the second user-facing surface is immediately adjacent to and in direct contact with the first non-user-facing surface with no intervening layers, and wherein the second layer is an acquisition/distribution layer (ADL) consisting of two sub-layers of different materials, wherein a first sub-layer is an apertured film acquisition layer and a second sub-layer is a non-woven distribution layer, wherein the first sub-layer is immediately adjacent to and in direct contact with the second sub-layer with no intervening sub-layers, and
wherein the apertured film acquisition layer includes perforations that form funnels configured to provide a circuitous path for fluid flow and oriented to prevent fluid flow back towards the first layer;
(iii) a third layer having a third user-facing surface and a third non-user-facing surface, wherein the third user-facing surface is immediately adjacent to and in direct contact with the second non-user-facing surface, and wherein the third layer is an absorbent core configured to receive and trap the fluid flowing from the second layer; and
(iv) a fourth layer having a fourth user-facing surface and a fourth non-user-facing surface, wherein the fourth user-facing surface is immediately adjacent to and in direct contact with the third non-user-facing surface with no intervening layers, wherein the fourth layer is a liquid impermeable barrier configured to contain the fluid received and trapped in the absorbent core while allowing air to transfer between the outside environment and the plurality of layers,
wherein each layer of the plurality of layers is at least 95% plant-based and does not include any petro-chemical derived materials.

\* \* \* \* \*